(12) United States Patent
Ihara et al.

(10) Patent No.: US 8,728,461 B2
(45) Date of Patent: May 20, 2014

(54) LACTIC ACID BACTERIUM HAVING HIGH IMMUNOGLOBULIN-A-INDUCING ABILITY

(75) Inventors: Yasuhiro Ihara, Tsukuba (JP); Hiroshi Murakami, Tsukuba (JP); Yoichi Takahagi, Tsukuba (JP)

(73) Assignee: Nippon Meat Packers, Inc., Osaka-Shi (JP)

( * ) Notice: Subject to any disclaimer, the term of this patent is extended or adjusted under 35 U.S.C. 154(b) by 468 days.

(21) Appl. No.: 13/001,337

(22) PCT Filed: Mar. 30, 2009

(86) PCT No.: PCT/JP2009/001430
§ 371 (c)(1),
(2), (4) Date: Dec. 23, 2010

(87) PCT Pub. No.: WO2010/001509
PCT Pub. Date: Jan. 7, 2010

(65) Prior Publication Data
US 2011/0104134 A1    May 5, 2011

(30) Foreign Application Priority Data
Jul. 4, 2008 (JP) .................. 2008-176172

(51) Int. Cl.
*A61K 35/74* (2006.01)
*A61P 31/00* (2006.01)
*A61P 37/02* (2006.01)
*C12N 1/20* (2006.01)

(52) U.S. Cl.
USPC ..................... 424/93.44; 435/253.4

(58) Field of Classification Search
None
See application file for complete search history.

(56) References Cited

PUBLICATIONS

Frece et al., "In vivo testing of functional properties of three selected probiotic strains", World Journal of Microbiology & Biotechnology, vol. 21, pp. 1401-1408 (2005).
Benyacoub et al., "*Enterococcus faecium* SF68 Enhances the Immune Response to *Giardia intestinalis* in Mice", Nutritional Immunology, pp. 1171-1176 (2005).
Benyacoub et al., "Supplementation of Food with *Enterococcus faecium* (SF68) Stimulates Immune Functions in Young Dogs", Nutritional Immunology, pp. 1158-1162 (2003).
PCT/IB/373 Form—International Preliminary Report on Patentability for PCT/JP2009/001430 (dated Feb. 17, 2011).

*Primary Examiner* — Lisa J Hobbs
(74) *Attorney, Agent, or Firm* — Edwards Wildman Palmer LLP; Peter F. Corless; Christopher R. Cowles

(57) ABSTRACT

A novel lactic acid bacterium strain is found, which has a high IgA production-inducing ability and a high immunostimulating activity, and belongs to the genus *Enterococcus*. Thus, provided is an excellent lactic acid bacterium preparation for foods or feeds, which has a high enteric colonization rate. Specifically disclosed are: a novel lactic acid bacterium *Enterococcus faecium* NHRD IHARA (FERM BP-11090) which has a high IgA production-inducing ability and a high immunostimulating activity; and a lactic acid bacterium preparation for enhancing the production of immunoglobulin A, which comprises a culture of the bacterium strain, an extract of the bacterium strain, or a product of any treatment of cells of the bacterium strain.

21 Claims, 10 Drawing Sheets

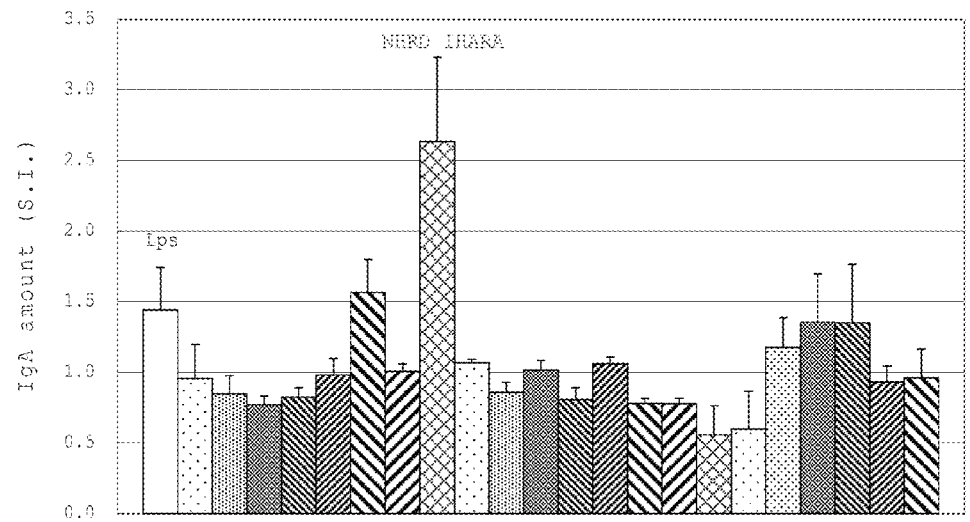
[Fig. 1A]

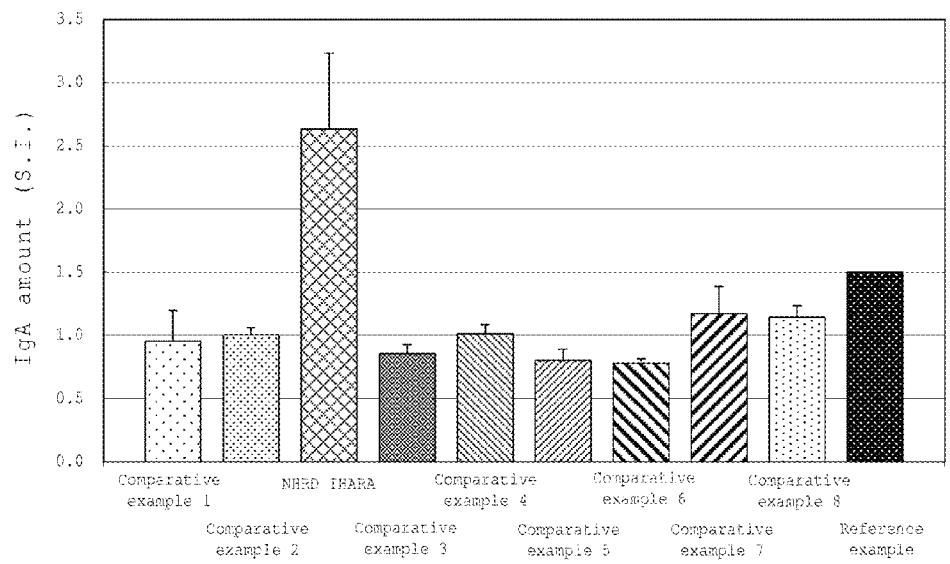

[Fig. 1B]

| | NHRD# | Group | Mouse data | | | |
|---|---|---|---|---|---|---|
| | | | Average | Standard deviation | Standard error | Number of data |
| Peyer's patch / E.faecium | 44 | Comparative example 1 | 0.9559024 | 0.4205732 | 0.2428209 | 3 |
| | 88 | Comparative example 2 | 1.0058214 | 0.0952827 | 0.0550115 | 3 |
| | IHARA | NHRD IHARA | 2.6348361 | 1.0366251 | 0.5984958 | 3 |
| | 99 | Comparative example 3 | 0.8576763 | 0.1220148 | 0.0704453 | 3 |
| | 102 | Comparative example 4 | 1.0141334 | 0.1749591 | 0.0714268 | 6 |
| | 104 | Comparative example 5 | 0.8045514 | 0.1514639 | 0.0874477 | 3 |
| Peyer's patch / E.faecalis | 199 | Comparative example 6 | 0.7814212 | 0.0580415 | 0.0335103 | 3 |
| | 326 | Comparative example 7 | 1.1739139 | 0.3677418 | 0.2123159 | 3 |
| | Commercial product | Comparative example 8 | 1.145541 | 0.1578402 | 0.0911291 | 3 |
| | NF-1011 strain | Reference example | 1.5 | | | |

[Fig. 2]
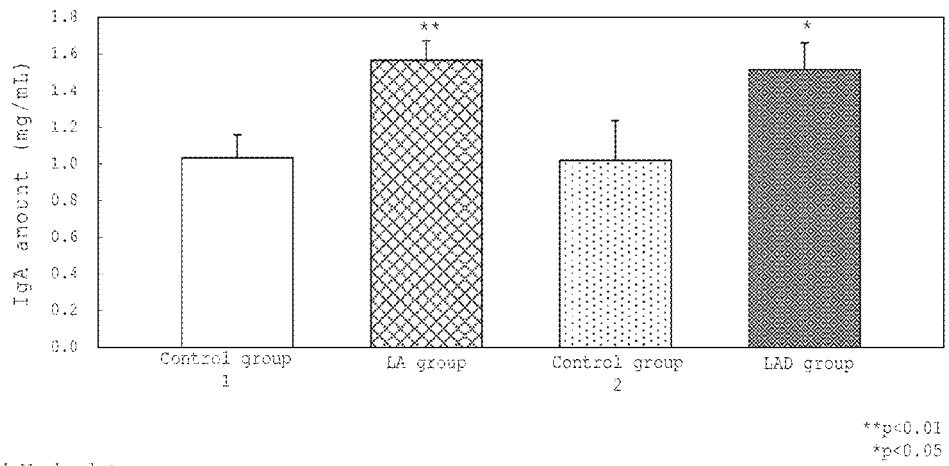
**p<0.01
*p<0.05
4 Weeks later
| Basis statistics | Control group 1 | LA group | Control group 2 | LAD group |
|---|---|---|---|---|
| Sample number | 16 | 17 | 17 | 18 |
| Average value | 1.033874444 | 1.567900000 | 1.021664667 | 1.515640000 |
| Sample standard deviation | 0.527023267 | 0.446196727 | 0.832356122 | 0.616046780 |
| Standard error | 0.124220575 | 0.105169577 | 0.214913427 | 0.145203619 |
[Fig. 3]
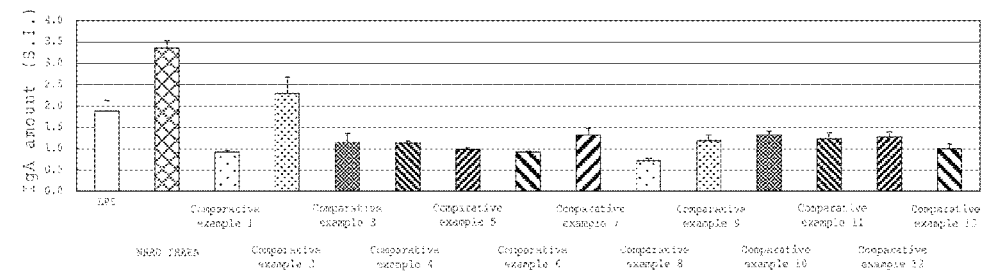

[Fig. 4]
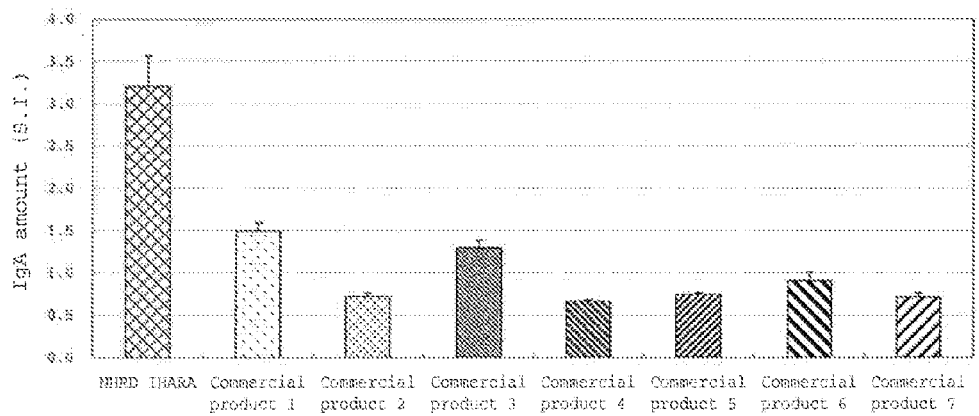

[Fig. 5A]

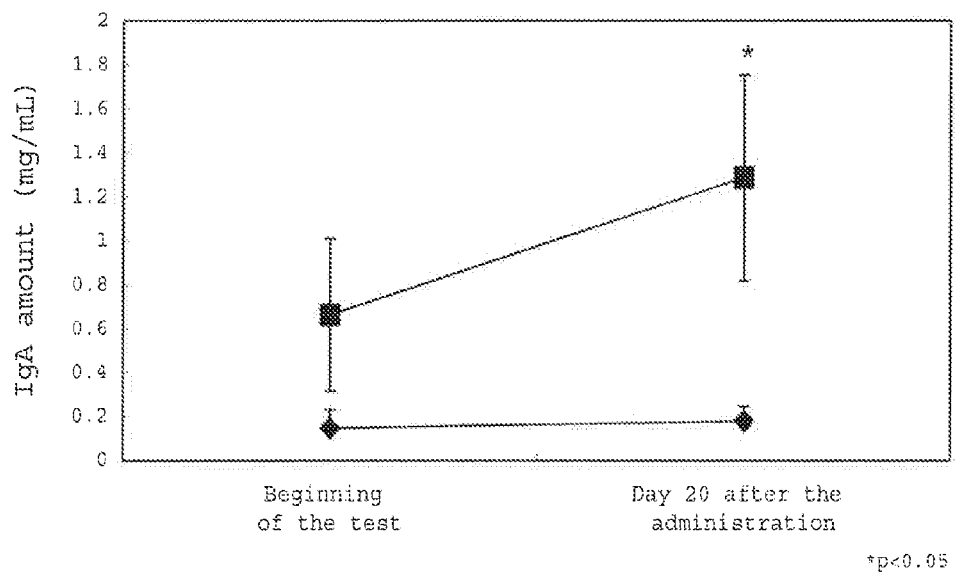

*p<0.05

Basic statistical values

| | | Beginning of the test | Day 20 after the administration |
|---|---|---|---|
| Control group | Average value | 0.14694612 | 0.17863128 |
| Test group | Average value | 0.6634269 | 1.2866519 |
| Control group | Standard error | 0.082436506 | 0.067279444 |
| Test group | Standard error | 0.346573435 | 0.468109621 |

IgA in excretions (=feces)—— at the end of first half growth period
Determination of the difference between grand mean;
2 samples with no response-t distribution-σ1=σ2

| Parameter | Test group | Control group | Difference |
|---|---|---|---|
| Sample number | 10 | 10 | 0 |
| Average | 1286651.9 | 178631.28 | 1108020.62 |
| Standard deviation | 1480292.597 | 212756.2836 | 1267536.313 |
| Degree of freedom | 18 | | |
| Statistical amount: t | 2.342935548 | | |
| P value | 0.030820948 | | |
| t (0.05/2) | 2.100923666 | | |
| Decision | Significant | | |

[Fig. 5B]

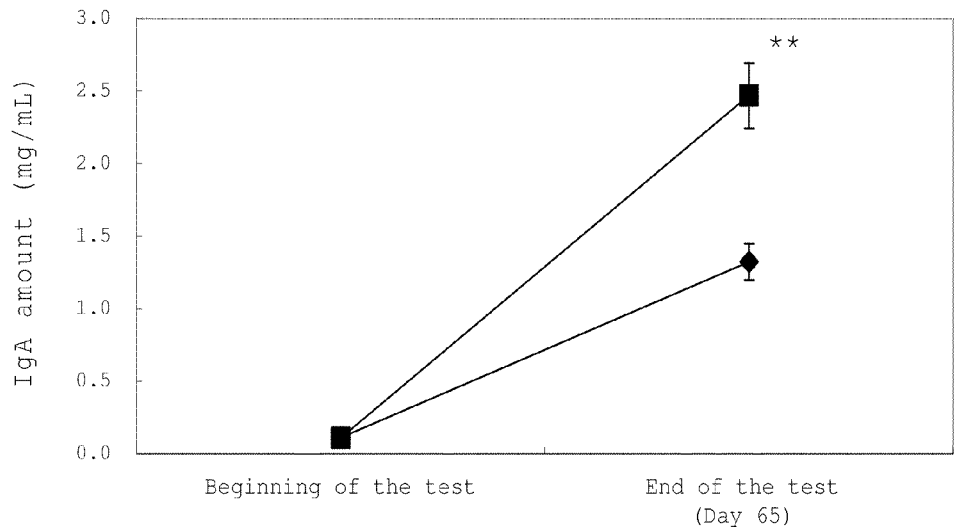

**p<0.01

Basic statistical values

|  |  | Beginning of the test | End of the test (Day 65) |
|---|---|---|---|
| Control group | Average value | 0.11174780 | 1.32396300 |
| Test group | Average value | 0.11081330 | 2.47022444 |
| Control group | Standard error | 0.00947151 | 0.12503244 |
| Test group | Standard error | 0.01503236 | 0.22423372 |

IgA in blood serum_ at the end of second half growth period

Determination of the difference between grand mean:
2 samples with no response·t distribution·σ1=σ2

| Parameter | Test group | Control group | Difference |
|---|---|---|---|
| Sample number | 9 | 10 | -1 |
| Average | 2470224.444 | 1323963 | 1146261.444 |
| Standard deviation | 672701.1698 | 395387.3039 | 277313.8658 |
| Degree of freedom | 17 |  |  |
| Statistical amount: t | 4.587644264 |  |  |
| P value | 0.000261864 |  |  |
| t (0.05/2) | 2.109818524 |  |  |
| Decision | Significant |  |  |

[Fig. 6A]
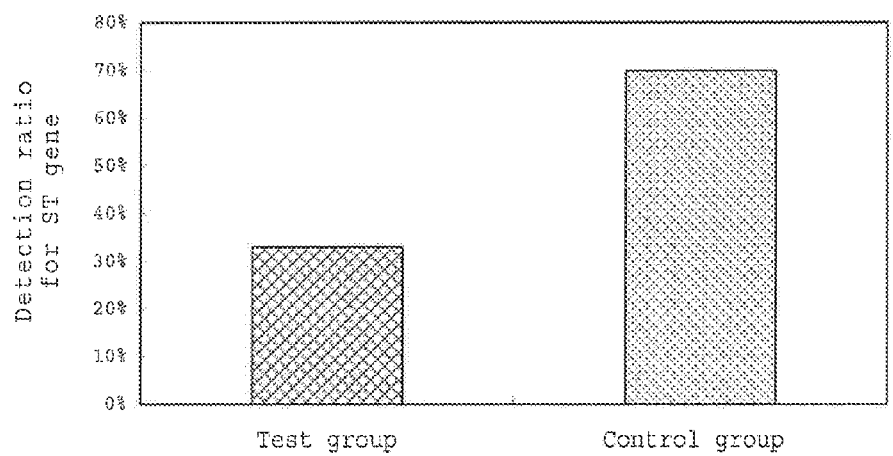

[Fig. 6B]
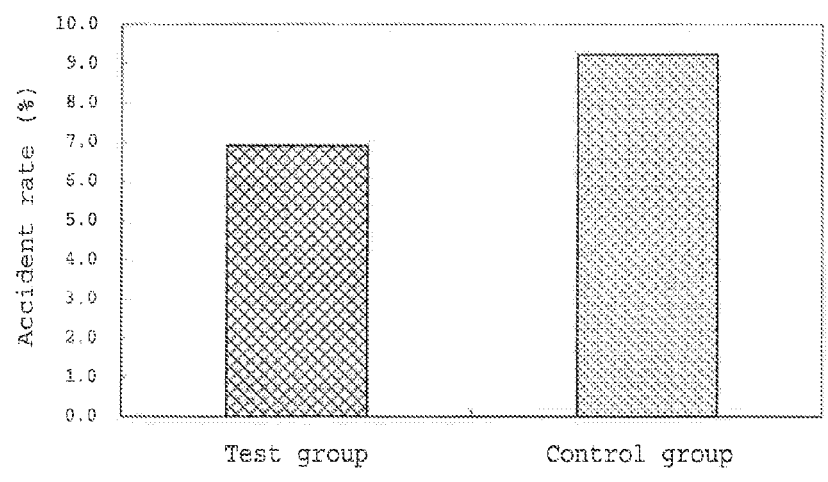

[Fig. 7A]
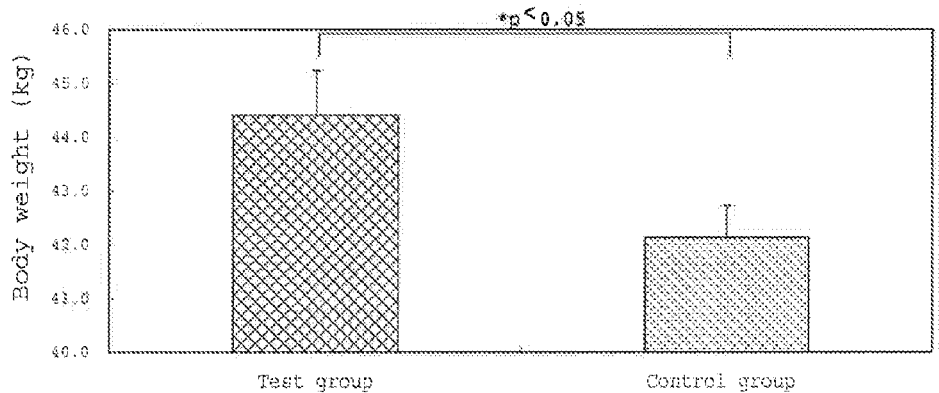
Body weight
| | Test group | Control group |
|---|---|---|
| Average value | 44.4192 | 42.1333 |
| Sample standard deviation | 2.8364 | 2.0519 |
| Standard error | 0.8198 | 0.5923 |
[Fig. 7B]
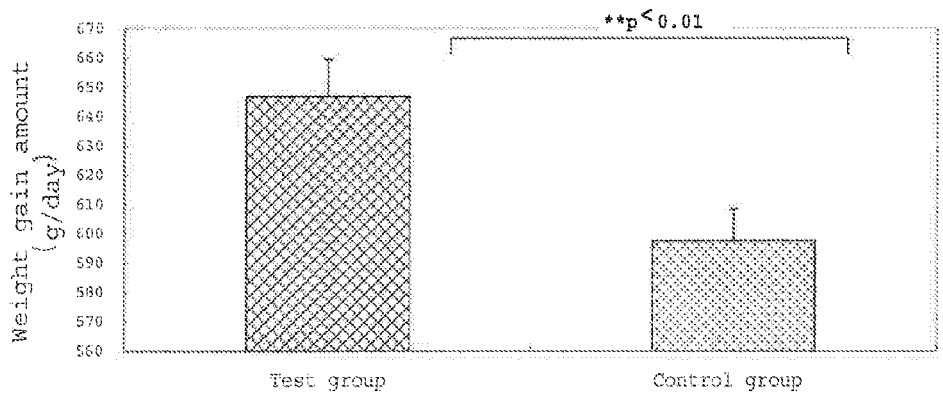
Weight gain amount for single day
| | Test group | Control group |
|---|---|---|
| Average value | 646.8708 | 597.7375 |
| Sample standard deviation | 43.6710 | 37.2801 |
| Standard error | 12.6067 | 10.7618 |

[Fig. 8]

```
E.faecium_IS-1.gnu        1 TTAAAGTTTGATCCTGGCTCAGGATGAACGCTGGCGGCGTGCCTAATACATGCAAGTCGT   60
E.faecium_NHRD89.gnu      1 -------------------------GACGAACGCTGGCGGCGTGCCTAATACATGCAAGTCGT   38

E.faecium_IS-1.gnu       61 ACGCTTCTTTTTCCACCGGAGCTTGCTCCACCGGAAAAAGAGGAGTGGCGAACGGGTGAG  120
E.faecium_NHRD89.gnu     39 ACGCTTCTTTTTCCACCGGAGCTTGCTCCACCGGAAAAAGAAGAGTGGCGAACGGGTGAG   98

E.faecium_IS-1.gnu      121 TAACACGTGGGTAACCTGCCCATCAGAAGGGGATAACACTTGGAAACAGGTGCTAATACC  180
E.faecium_NHRD89.gnu     99 TAACACGTGGGTAACCTGCCCATCAGAAGGGGATAACACTTGGAAACAGGTGCTAATACC  158

E.faecium_IS-1.gnu      181 GTATAACAATCGAAACCGCATGGTTTTGATTTGAAAGGCGCTTTCGGGTGTCGCTGATGG  240
E.faecium_NHRD89.gnu    159 GTATAACAATCGAAACCGCATGGTTTTGATTTGAAAGGCGCTTTCGGGTGTCGCTGATGG  218

E.faecium_IS-1.gnu      241 ATGGACCCGCGGTGCATTAGCTAGTTGGTGAGGTAACGGCTCACCAAGGCCACGATGCAT  300
E.faecium_NHRD89.gnu    219 ATGGACCCGCGGTGCATTAGCTAGTTGGTGAGGTAACGGCTCACCAAGGCCACGATGCAT  278

E.faecium_IS-1.gnu      301 AGCCGACCTGAGAGGGTGATCGGCCACATTGGGACTGAGACACGGCCCAAACTCCTACGG  360
E.faecium_NHRD89.gnu    279 AGCCGACCTGAGAGGGTGATCGGCCACATTGGGACTGAGACACGGCCCAAACTCCTACGG  338

E.faecium_IS-1.gnu      361 GAGGCAGCAGTAGGGAATCTTCGGCAATGGACGAAAGTCTGACCGAGCAACGCCGCGTGA  420
E.faecium_NHRD89.gnu    339 GAGGCAGCAGTAGGGAATCTTCGGCAATGGACGAAAGTCTGACCGAGCAACGCCGCGTGA  398

E.faecium_IS-1.gnu      421 GTGAAGAAGGTTTTCGGATCGTAAAACTCTGTTGTTAGAGAAGAACAAGGATGAGAGTAA  480
E.faecium_NHRD89.gnu    399 GTGAAGAAGGTTTTCGGATCGTAAAACTCTGTTGTTAGAGAAGAACAAGGATGAGAGTAA  458

E.faecium_IS-1.gnu      481 CTGTTCATCCCTTGACGGTATCTAACCAGAAAGCCACGGCTAACTACGTGCCAGCAGCCG  540
E.faecium_NHRD89.gnu    459 CTGTTCATCCCTTGACGGTATCTAACCAGAAAGCCACGGCTAACTACGTGCCAGCAGCCG  518

E.faecium_IS-1.gnu      541 CGGTAATACGTAGGTGGCAAGCGTTGTCCGGATTTATTGGGCGTAAAGCGAGCGCAGGCG  600
E.faecium_NHRD89.gnu    519 CGGTAATACGTAGGTGGCAAGCGTTGTCCGGATTTATTGGGCGTAAAGCGAGCGCAGGCG  578

E.faecium_IS-1.gnu      601 GTTTCTTAAGTCTGATGTGAAAGCCCCCGGCTCAACCGGGGAGGGTCATTGGAAACTGGG  660
E.faecium_NHRD89.gnu    579 GTTTCTTAAGTCTGATGTGAAAGCCCCCGGCTCAACCGGGGAGGGTCATTGGAAACTGGG  638

E.faecium_IS-1.gnu      661 AGACTTGAGTGCAGAAGAGGAGAGTGGAATTCCATGTGTAGCGGTGAAATGCGTAGATAT  720
E.faecium_NHRD89.gnu    639 AGACTTGAGTGCAGAAGAGGAGAGTGGAATTCCATGTGTAGCGGTGAAATGCGTAAATAT  698

E.faecium_IS-1.gnu      721 ATGGAGGAACACCAGTGGCGAAGGCGGCTCTCTGGTCTGTAACTGACGCTGAGGCTCGAA  780
E.faecium_NHRD89.gnu    699 ATGGAGGAACACCAGTGGCGAAGGCGGCTCTCTGGTCTGTAACTGACGCTGAGGCTCGAA  758

E.faecium_IS-1.gnu      781 AGCGTGGGGAGCAAACAGGATTAGATACCCTGGTAGTCCACGCCGTAAACGATGAGTGCT  840
E.faecium_NHRD89.gnu    759 AGCGTGGGGAGCAAACAGGATTAGATACCCTGATAGTCCACGCCGTAAACGATGAGTGCT  818

E.faecium_IS-1.gnu      841 AAGTGTTGGAGGGTTTCCGCCCTTCAGTGCTGCAGCTAACGCATTAAGCACTCCGCCTGG  900
E.faecium_NHRD89.gnu    819 AAGTGTTGGAGGGTTTCCGCCCTTCAGTGCTGCAGCTAACGCATTAAGCACTCCGCCTGG  878

E.faecium_IS-1.gnu      901 GGAGTACGACCGCAAGGTTGAAACTCAAAGGAATTGACGGGGGCCCGCACAAGCGGTGGA  960
E.faecium_NHRD89.gnu    879 GGAGTACGACCGCAAGGTTGAAACTCAAAGGAATTGACGGGGGCCCGCACAAGCGGTGGG  938

E.faecium_IS-1.gnu      961 GCATGTGGTTTAATTCGAAGCAACGCGAAGAACCTTACCAGGTCTTGACATCCTTTGACC 1020
E.faecium_NHRD89.gnu    939 GCATGTGGTTTAATTCGAAGCAACGCGAAGAACCTTACCAGGTCTTGACATCCTTTGACC  998

E.faecium_IS-1.gnu     1021 ACTCTAGAGATAGAGCTTCCCCTTCGGGGGCAAAGTGACAGGTGGTGCATGGTTGTCGTC 1080
E.faecium_NHRD89.gnu    999 ACTCTAGAGATAGAGCTTCCCCTTCGGGGGCAAAGTGACAGGTGGTGCATGGTTGTCGTC 1058

E.faecium_IS-1.gnu     1081 AGCTCGTGTCGTGAGATGTTGGGTTAAGTCCCGCAACGAGCGCAACCCTTATTGTTAGTT 1140
E.faecium_NHRD89.gnu   1059 AGCTCGTGTCGTGAGATGTTGGGTTAAGTCCCGCAACGAGCGCAACCCTTATTGTTAGTT 1118

E.faecium_IS-1.gnu     1141 GCCATCATTCAGTTGGGCACTCTAGCAAGACTGCCGGTGACAAACCGGAGGAAGGTGGGG 1200
E.faecium_NHRD89.gnu   1119 GCCATCATTCAGTTGGGCACTCTAGCAAGACTGCCGGTGACAAACCGGAGGAAGGTGGGG 1178

E.faecium_IS-1.gnu     1201 ATGACGTCAAATCATCATGCCCCTTATGACCTGGGCTACACACGTGCTACAATGGGAAGT 1260
E.faecium_NHRD89.gnu   1179 ATGACGTCAAATCATCATGCCCCTTATGACCTGGGCTACACACGTGCTACAATGGGAAGT 1238

E.faecium_IS-1.gnu     1261 ACAACGAGTTGCGAAGTCGCGAGGCTAAGCTAATCTCTTAAAGCTTCTCTCAGTTCGGAT 1320
E.faecium_NHRD89.gnu   1239 ACAACGAGTTGCGAAGTCGCGAGGCTAAGCTAATCTCTTAAAGCTTCTCTCAGTTCGGAT 1298

E.faecium_IS-1.gnu     1321 TGCAGGCTGCAACTCGCCTGCATGAAGCCGGAATCGCTAGTAATCGCGGATCAGCACGCC 1380
E.faecium_NHRD89.gnu   1299 TGCAGGCTGCAACTCGCCTGCATGAAGCCGGAATCGCTAGTAATCGCGGATCAGCACGCC 1358

E.faecium_IS-1.gnu     1381 GCGGTGAATACGTTCCCGGGCCTTGTACACACCGCCCGTCACACCACGAGAGTTTGTAAC 1440
E.faecium_NHRD89.gnu   1359 GCGGTGAATACGTTCCCGGGCCTTGTACACACCGCCCGTCACACCACGAGAGTTTATAAC 1418

E.faecium_IS-1.gnu     1441 ACCCGAAGTCGGTGAGGTAACC-------------------------------------- 1462
E.faecium_NHRD89.gnu   1419 ACCCGAAGTCGGTGAGGTAACCTTTTTGGAGCCAGCCGCCTAAGGTGGGATAGATGATTG 1478

E.faecium_IS-1.gnu     1462 --------------------------------                              1462
E.faecium_NHRD89.gnu   1479 GGGTGAAGTCGTAACAAGGTAGCCGTATCGGAA                             1511
```

LACTIC ACID BACTERIUM HAVING HIGH IMMUNOGLOBULIN-A-INDUCING ABILITY

CROSS-REFERENCES TO RELATED APPLICATIONS

This application is a 35 U.S.C. §371 U.S. national entry of International Application PCT/JP2009/001430 (WO 2010/001509) having an International filing date of Mar. 30, 2009, which claims under 35 U.S.C. §119(a) the benefit of Japanese Application No. 2008-176172, filed Jul. 4, 2008, the entire contents of which are incorporated herein by reference.

TECHNICAL FIELD

A novel lactic acid bacterium which has a high ability of inducing immunoglobulin A and an immunostimulating activity, and a lactic acid bacterium preparation including the lactic acid bacterium.

BACKGROUND ART

A living body continuously introduces a foreign material (i.e., an antigen material) to the inside of the body by physiological actions like breathing or eating that are essential for maintaining biological activities. As a result, surface of a respiratory organ or a digestive tract of a living body is constantly exposed to an antigen material and bacteria or viruses, and allergens originating from pollen and food, etc. having a pathogenic property may be included therein. In other words, on the surface of a respiratory organ or a digestive tract, a living body remains constantly exposed to pathogenic microorganisms and allergens.

Accordingly, in response to various invading antigen materials, a living body has an immune response system which can distinguish favorable ones from unfavorable ones and exclude them depending on necessity. The immune system found on the surface of a respiratory organ or a digestive tract as a front-end defense mechanism is mucosal immune.

As a key player for the mucosal immune system, the material responsible for preventing attachment of pathogenic microorganisms or invasion and absorption of allergens to a living body is immunoglobulin A (hereinafter, also referred to as "IgA"), which is one type of immunoglobulins.

IgA plays an important role of neutralizing bacteria or viruses, inhibiting their attachment to biological tissues, and inhibiting allergy caused by food antigen, etc., and as an IgA-inducing tissue, Peyer's patch is present in an intestinal canal.

It is known that babies, elderly and people with poor health have a weak immunity, and therefore exhibit low resistance to foreign materials from the outside like pathogens. In addition to this, it is also reported that humans nowadays have a reduced enteric mucosal immune due to stress caused by a change in living environments, etc., and as a result allergic diseases are dramatically increased (Non-Patent Document 1).

Thus, if IgA production from mucosa of a living body is enhanced, immunity on the surface of mucosa of an intestinal canal, etc. can be increased, and therefore it is expected that infection by pathogenic microorganisms or occurrence of allergic reaction can be effectively prevented.

Meanwhile, under the purpose of providing an animal protein to human beings, in the field of livestock farming, livestock is raised as an animal with an economical benefit, and a raising style which values so-called productivity like increasing body weight or enhancing maturity, etc. has been conventionally adopted. In addition to the purpose of enhancing the productivity, vaccination or addition of antibiotics to animal feeds has been actively carried out to prevent an outbreak of diseases, etc from the view point of enhancing hygiene level of a livestock product as a food.

In recent years, in addition to the raising style described above, stockbreeding management is transformed into large-scale management form which pursues an economic value according to efficiencies obtained from mechanization and a scale merit by raising a great number of animals.

Thus, although the recent livestock management made it possible to provide stable supply of low-price livestock products to consumers, it is also true that the livestock is put into a stressful environment like less area for breeding and more possibilities of vaccination.

In addition to the situations described above, secondary infection by bacteria like *E. coli* increases now more than ever in current livestock breeding due to the emergence of pathogenic viruses which inhibit an immune function of a living body (Non-Patent Document 2).

In livestock breeding, occurrence of a disease like diarrhea causes an increase in accident rate or a reduction in body weight gain, therefore yielding low productivity. In particular, since young animals are prone to suffer from diseases and it results in a significant economic loss, it is important to prevent the occurrence of disease as much as possible. In this regard, the use of antibiotics is rather limited due to the concern regarding the emergence of antibiotic-resistant bacteria, etc. Thus, as a measure for dealing with the frequent diseases, the use of antibiotics is now very carefully considered by livestock breeders. In this connection, it is now livestock breeders' wish to have the development of animal feeds or feed additives having an antibiotic-like activity that are originated from natural products and can replace antibiotics.

In order to solve the above problems, it would be very useful if a substance which is safe and has an activity of increasing immunity of a living body and enhancing resistance is found from natural products and is used as food products, animal feeds or pharmaceutical agents. In this regard, since IgA is a substance which plays a key role in immunological mechanism on surface of mucosa, it is desired to develop food products or animal feeds which can increase the production amount of IgA and activate the immunity of a living body.

Meanwhile, it has long been known that the lactic acid bacteria have probiotic effects. As one of the effects, it is known that the bacteria body has an immunostimulating effect (Non-Patent Document 3).

In the field of livestock breeding, many studies are being carried out based on the idea that the immunostimulating effects of the lactic acid bacteria can increase resistance against diseases (Non-Patent Document 7).

As for the lactic acid bacteria which can induce IgA production, that is one of the immunostimulating effects, there are reports regarding Bifidus bacteria in addition to the lactic acid bacteria belonging to the genus *Lactobacillus*, the genus *Leuconostoc* and the genus *Pediococcus* originating from a plant (Patent Documents 1 and 2) or *Enterococcus* bacteria (Patent Documents 3 to 5).

It can be generally said that colonization rate of the lactic acid bacteria originating from a plant is not high in a body of an animal like human. Further, being an obligate anaerobe, Bifidus bacteria need a special environment for culture condition, i.e., anaerobic culture. In addition, there are also bacterium strains which require nutrients like special amino acids, vitamins and metal ions as a component for medium, and therefore the artificial culture medium becomes to have a complicate composition (Non-Patent Document 4). In addition, as being an obligate anaerobe, they cannot grow under normal environmental condition having oxygen, and there is also a problem in viability and stability when prepared in a preparation.

Meanwhile, the lactic acid bacteria belonging to the genus *Enterococcus* are the lactic acid bacteria which are present in the gut of mammals. Being a facultative anaerobe, they do not require special culture condition like Bifidus bacterium and are suitable for large-scale culture as they are a bacterial species which can propagate in a medium having relatively simple composition. Furthermore, as the culture in the presence of oxygen is possible, their viability and stability under normal environmental condition are higher than those of Bifidus bacterium. Furthermore, considering that they are the lactic acid bacteria which are originally present in the gut of mammals, it is expected that they have higher colonization rate than other lactic acid bacteria originating from a plant when they are orally administered to a human or an animal.

In addition, it has been already known that some bacterium strains of the *Enterococcus* bacteria have immunostimulating effects and are used as an agent for preventing infections against microbes having resistance to pharmaceutical agents (Patent Documents 3 to 5) and the bacterium strains having immunostimulating effects according to increased production of IgA have been reported (Patent Document 5), and also an immunostimulating agent, an anti-cancer agent and various preparations for allergy are suggested.

However, the lactic acid bacteria belonging to the genus *Enterococcus* as used in the lactic acid bacterium preparation of Patent Document 5 are *Enterococcus faecalis* and the production amount of IgA induced by the bacterium strain is less than twice the negative control, which cannot be said to be sufficient.

*Enterococcus faecium*, which is one type of the bacteria belonging to the genus *Enterococcus*, is a bacterial species that has been conventionally and widely used as a medicine for intestinal disorders or an additive for animal feeds. Thus, based on the fact that it has no problem in terms of safety and enteric colonization and the technology required for the large scale culture has been already established, if it becomes possible to use it as a lactic acid bacterium preparation having immunostimulating effects for pharmaceutical products, food products or animal feeds, it is believed to be one of the hopeful lactic acid bacteria being extremely useful from the economical point of view, as well as the safety and immune function enhancing effects described above.

However, until now there is almost no report regarding the induction of IgA production in *Enterococcus faecium*. Although Patent Documents 6 and 7 describe that Enterococcus faecium has an activity of inducing IgA production, the one that is actually determined as an activity of inducing IgA production is an indirect determination based on a property change in Peyer's patch (i.e., IgA antibody). Thus, no quantitative determination on effectiveness is made and also it cannot be said that the IgA production-inducing ability itself is sufficient.

Furthermore, regarding any of the lactic acid bacteria of the genus *Enterococcus* described above, no determination was made on the immunostimulating effects that are based on the effect of inhibiting colonization of pathogenic substances or the effect of increasing productivity of livestock, and therefore verification of the effectiveness is insufficient.

[Patent Document 1] Japanese Patent Application Laid-Open (JP-A) No. 2007-308419

[Patent Document 2] JP-A No. 2-280059

[Patent Document 3] Japanese Patent No. 3151442

[Patent Document 4] JP-A No. 2006-89421

[Patent Document 5] JP-A No. 11-92389

[Patent Document 6] JP-A No. 2003-113114

[Patent Document 7] JP-A No. 2006-67881

[Non-Patent Document 1] "Front line of the mucosal immunology," Yasunobu Yoshikai ed., pages 116 to 129, published by Medicinal and Dental Journal Publications

[Non-Patent Document 2] "Measures for swine disease in actual field," written by Hiromichi Ishikawa, pages 13 to 16, published by Benet, Ltd.

[Non-Patent Document 3] "Intestinal flora and infection•immunity," Tomotari Mitsuoka ed., pages 156 to 158, published by Publication center of the academic society

[Non-Patent Document 4] "Sciences of fermented milk," Akiyoshi Hosono ed., pages 217 to 223, published by I•K corporation

[Non-Patent Document 5]Yakugaku Zasshi, Vol. 112, No. 12, pages 919 to 925, 1992

[Non-Patent Document 6]Modern media, Vol. 52, No. 7, pages 209 to 216, 2006

[Non-Patent Document 7] "Health functions and applications of lactic acid bacteria," reviewed by Shuichi Kaminogawa, pages 306 to 312, CMC publications

DISCLOSURE OF THE INVENTION

Problems to be Solved by the Invention

An object of the present invention is to find out a bacterium strain of novel lactic acid bacterium belonging to the genus *Enterococcus* which has a high IgA production-inducing ability and a high immunostimulating activity, as well as to provide a lactic acid bacterium preparation having a high enteric colonization rate that can be used for better food products, animal feeds or pharmaceutical products.

Means for Solving the Problems

Thus, as a result of carrying out intensive studies by screening bacterium strains having an IgA production-inducing ability against the bacteria of the genus *Enterococcus*, inventors of the present invention found out the novel lactic acid bacterium strain *Enterococcus faecium* NHRD IHARA belonging to the genus *Enterococcus* which has a high IgA production-inducing ability.

Based on the mycological properties (Table 1) and sequence analysis of r-RNA, NHRD IHARA (FERM BP-11090) of the invention was identified as a novel lactic acid bacterium belonging to *Enterococcus faecium*, and its IgA inducing ability is significantly excellent compared to other known *Enterococcus faecium*, and therefore the invention was completed.

Furthermore, the inventors of the invention confirmed that the lactic acid bacterium preparation having NHRD IHARA of the invention has an excellent effect of inhibiting the enteric colonization of pathogenic substances in the gut and enhancing the productivity of livestock, and thus also completed the invention relating to the food products, animal feeds and an agent for increasing immunity, etc. in which the lactic acid bacterium preparation of the invention is used.

Specifically, the present invention is related to the followings.

[1] *Enterococcus faecium* NHRD IHARA (FERM BP-11090).

[2] The bacterium strain according to the above [1], which is a lactic acid bacterium that can enhance the production of immunoglobulin A and inhibit the proliferation of a pathogenic bacterium in a living body.

[3] A lactic acid bacterium preparation having an immunoglobulin A production-enhancing activity in a living body, comprising a culture of the bacterium strain according to the above [1] or [2], an extract of the bacterium strain, or a treatment product of cells of the bacterium strain.

[4] The lactic acid bacterium preparation according to the above [3], further comprising other lactic acids, lactic acid preparations, *bifidobacterium, bifidobacterium* preparations, other microorganisms and other microorganism preparations having an immunoglobulin A production-enhancing activity in a living body.

[5] An additive for a food and beverage product comprising the lactic acid bacterium preparation according to the above [3] or[4] as an effective component for enhancing immunoglobulin A production in a living body.

[6] A food and beverage product comprising the lactic acid bacterium preparation according to the above [3] or [4] as an effective component for enhancing immunoglobulin A production in a living body.

[7] An additive for animal feeds comprising the lactic acid bacterium preparation according to the above [3] or [4] as an effective component for enhancing immunoglobulin A production in a living body.

[8] The additive for animal feeds according to the above [7], which is used for increasing body weight, enhancing body weight gain or reducing accident rate of livestock.

[9] Animal feeds comprising the lactic acid bacterium preparation according to the above [3] or [4] as an effective component for enhancing immunoglobulin A production in a living body.

[10] An agent for enhancing immune function for a human or an animal, comprising the lactic acid bacterium preparation according to the above [3] or [4] and a pharmaceutically acceptable carrier or additive.

[11] A pharmaceutical composition for preventing or treating an infection in a human or an animal, comprising the lactic acid bacterium preparation according to the above [3] or [4] and a pharmaceutically acceptable carrier or additive.

[12] A method of increasing body weight of livestock, wherein the lactic acid bacterium preparation according to the above [3] or [4] is used.

[13] A method of enhancing body weight gain of livestock, wherein the lactic acid bacterium preparation according to the above [3] or [4] is used.

[14] A method of reducing an accident of livestock, wherein the lactic acid bacterium preparation according to the above [3] or [4] is used.

[15] A method of improving an immune function of an animal (excluding a human), wherein the lactic acid bacterium preparation according to the above [3] or [4] is used.

[16] A method of inhibiting an infection of an animal (excluding a human), wherein the lactic acid bacterium preparation according to the above [3] or [4] is used.

Effects of the Invention

*Enterococcus faecium* NHRD IHARA (FERM BP-11090), which is the novel lactic acid bacterium strain of the invention, has a high IgA production-inducing ability, a high enteric colonization rate in the gut and high immunostimulating effects. Therefore, when added as a lactic acid bacterium preparation to food products, animal feeds and the like, it can provide an effect of enhancing the immunity of an animal including human and livestock. Moreover, it can be used as an agent for enhancing an immune function and a pharmaceutical composition for preventing and treating infections.

BRIEF DESCRIPTION OF THE DRAWINGS

FIG. 1A shows the production amount of IgA from various bacterium strains during the screening, indicating the IgA production-inducing activity of a mouse Peyer' s patch cell. In addition, the positive control (LPS) indicates a case in which no addition was made. In addition, each value was expressed as an average value obtained from at least three repeating measurements by using a mouse Peyer's patch.

FIG. 1B indicates the IgA production-inducing activity of a mouse Peyer's patch cell. Other bacterium strains belonging to the same *Enterococcus faecium* as in FIG. 1A and still other bacterium strains belonging to other species of the genus *Enterococcus* were used and shown as Comparative examples 1 to 5 and Comparative examples 6 to 8, respectively, along with bacterium strain of the invention. Comparative example 1 (NHRD44), Comparative example 2 (NHRD88), Comparative example 3 (NHRD99), Comparative example 4 (NHRD102), Comparative example 5 (NHRD104), Comparative example 6 (NHRD199), Comparative example 7 (NHRD326) and Comparative example 8 (commercially available probiotics). Reference example: Example 1 of Patent Document 5 (*Enterococcus faecalis* NF-1011). In addition, each value was expressed as an average value obtained from at least three repeating measurements by using a mouse Peyer's patch.

FIG. 2 shows the production amount of IgA when the bacterium strain of the invention is orally administered to a mouse.

(1) Control group 1 (a group to which *Enterococcus faecium* is not administered)

(2) Control group 2 (a group administered with *Enterococcus faecium* in which the S.I. is around 1 in Example 3)

(3) A group administered with dried vital cells of *Enterococcus faecium* NHRD IHARA (LA)

(4) A group administered with dried dead cells of *Enterococcus faecium* NHRD IHARA (LAD)

FIG. 3 indicates the IgA production-inducing activity of a pig Peyer's patch cell. Herein, Comparative examples 1 to 8 represent the same bacterium strain as those of FIG. 1 and other bacterium strains belonging to the genus Enterococcus (*Enterococcus faecalis*) were shown as Comparative examples 9 to 13. Comparative example 9 (NHRD42), Comparative example 10 (NHRD54), Comparative example 11 (NHRD64), Comparative example 12 (NHRD248) and Comparative example 13 (NHRD249). In addition, each value was expressed as an average value obtained from at least three repeating measurements by using a pig Peyer's patch.

FIG. 4 shows the IgA production-inducing ability of the bacterium strain of the invention compared to the lactic acid bacterium preparations that are commercially available in the field of livestock breeding and other microbial preparations. In addition, each value was expressed as an average value obtained from at least three repeating measurements by using a pig Peyer's patch. Herein, commercially available product 1 indicates *Bacillus subtilis*, commercially available product 2 indicates *Clostridium butyricum*, commercially available product 3 indicates the microbe of the genus *Bacillus*, commercially available product 4 indicates the microbe of the genus *Lactobacillus*, commercially available product 5 indicates *Enterococcus faecium*, commercially available product 6 indicates *Clostridium butyricum* and commercially available product 7 indicates *Enterococcus faecalis*.

FIG. 5A shows the change in the average value of IgA amount until the end of the test, in which the IgA amount was measured for the test group and the control group each having 1,200 pigs. Specifically, ten animals were selected from each test group and the average value of the IgA amount in the animal feces was obtained. ■ represents the test group and ♦ represents the control group.

FIG. 5B shows the change in the average value of IgA amount until the end of the test, in which the IgA amount was measured for the test group and the control group each having 1,200 pigs. Specifically, ten animals were selected from each test group and the average value of the IgA amount in the blood serum was obtained. ■ represents the test group and ♦ represents the control group.

FIG. 6A shows the ETEC infection rate after 65 days in a real hog farm. The test group and the control group each have 1,200 pigs. The animals of the test group received the vital cells of the bacterium strain of the invention in an amount of $10^{10}$ cells per day per animal simultaneously with the ETEC infection. Thereafter, the average value of heat-resistant enterotoxin (ST) gene detected from the feces was measured, and the infection rate after 65 days was obtained.

FIG. 6B shows the ETEC accident rate after 65 days in a real hog farm. The test group and the control group each have 1,200 pigs. The animals of the test group received the vital cells of the bacterium strain of the invention in an amount of $10^{10}$ cells per day per animal simultaneously with the ETEC infection. Thereafter, the accident rate after 65 days was obtained.

FIG. 7A shows the change in weight gain rate between the test group and the control group that are the same as those of FIG. 6A and FIG. 6B.

FIG. 7B shows the change in increased amount between the test group and the control group that are the same as those of FIG. 6A and FIG. 6B.

FIG. 8 shows the homology between the IS-1 strain belonging to *Enterococcus faecium* (Patent Document 5) and the sequence of 16srRNA gene from 5' end to the base at position 1511 (homology of 99.7%).

THE BEST MODES FOR CARRYING OUT THE INVENTION

1. Microorganism Related to the Invention

The novel microorganism of the invention is *Enterococcus faecium* NHRD IHARA, which is the lactic acid bacterium belonging to *Enterococcus faecium* and has been deposited in Japan with Patent Microorganism Depository Center of National Institute of Advanced Industrial Science and Technology (AIST) located at 1-1-1, Higashi, Tsukuba, Ibaraki, Japan with the microorganism name of *Enterococcus faecium* NHRD89 and deposit number of FERM P-21592 on June 6, 2008. On Feb. 2, 2009, the microorganism name was changed to Enterococcus faecium NHRD IHARA and transferred to the International Depository Organization at Budapest, and internationally deposited under the international deposit number of FERM BP-11090.

<Mycological Properties>

The mycological properties of *Enterococcus faecium* NHRD IHARA of the invention are as described in Table 1.

TABLE 1

| | Bacterial strain of the invention *Enterococcus faecium* NHRD IHARA |
|---|---|
| Morphology | Coccus |
| Gram staining property | Positive |
| Spore | Not formed |
| Motility | − |
| Behavior toward oxygen | Facultatively anaerobic |
| Catalase reaction | − |
| Generation of gas from glucose | − |
| Growth at 10° C. | + |
| Growth at 45° C. | + |
| Growth at 50° C. | + |
| Growth in the presence of 6.5% NaCl | + |
| Growth at pH 9.6 | + |
| Growth in the presence of 40% bile | + |
| Yellow pigment formation | − |
| Arginine dihydrolase | + |
| Hydrolysis of hippuric acid | + |
| Hydrolysis of esculin | + |
| Metabolism of sugars | |
| L-Xylose | + |
| D-Xylose | − |
| Sucrose | + |
| Lactose | + |
| Melibiose | + |
| Raffinose | − |
| Melicitose | − |
| Glycerol | − |
| Adonitol | − |
| Mannitol | + |
| D-Arabinose | − |
| L-Arabinose | + |
| D-Ribose | + |
| D-Glucose | + |
| D-Fructose | + |
| D-Mannose | + |
| D-Galactose | + |
| D-Mannitol | + |
| L-Sorbose | − |
| D-Sorbitol | − |
| L-Rhamnose | − |
| Amygdalin | + |
| Esculin | + |
| Cellobiose | + |
| Inulin | − |
| Melezitose | + |

In the table, "+" indicates positive and "−" indicates negative.

The sugar-metabolic property of the bacterium strain of the invention for specific sacccharides (L-xylose, melibiose) is different from that of typical standard strain *Enterococcus faecium*; JCM 5804. In addition, the sugar-metabolic property of the bacterium strain of the invention for raffinose and D-sorbitol is also different from that of the *Enterococcus faecium* IS-1 strain used in the publication of JP-A No. 2006-67881.

Mycological properties of the bacterium strain of the invention compared to *Enterococcus faecium* IS-1 and the typical standard strain *Enterococcus faecium* JCM 5804 are as described in Table 2.

TABLE 2

| | Bacterial strain of the invention *Enterococcus* NHRD IHARA | JP-A No. 2006-67881 *Enterococcus* IS-1 strain | Standard strain *Enterococcus* JCM 5804 strain |
|---|---|---|---|
| Morphology | Coccus | Coccus | Coccus |
| Gram staining property | Positive | Positive | Positive |
| Spore | Not formed | Not formed | Not formed |
| Motility | − | − | − |

TABLE 2-continued

| | Bacterial strain of the invention *Enterococcus* NHRD IHARA | JP-A No. 2006-67881 *Enterococcus* IS-1 strain | Standard strain *Enterococcus* JCM 5804 strain |
|---|---|---|---|
| Behavior toward oxygen | Facultatively anaerobic | Facultatively anaerobic | Facultatively anaerobic |
| Catalse reaction | − | − | − |
| Generation of gas from glucose | − | − | − |
| Growth at 10° C. | + | + | + |
| Growth at 45° C. | + | + | + |
| Growth at 50° C. | + | + | + |
| Growth in the presence of 6.5% NaCl | + | + | + |
| Growth at pH 9.6 | + | + | + |
| Growth in the presence of 40% bile | + | + | + |
| Yellow pigment formation | − | − | − |
| Arginine dihydrolase | + | + | + |
| Hydrolysis of hippuric acid | + | + | + |
| Hydrolysis of esculin | + | + | + |
| Metabolism of sugars | | | |
| L-Xylose | + | ND | − |
| D-Xylose | − | − | − |
| Sucrose | + | + | + |
| Lactose | + | + | + |
| Melibiose | + | + | − |
| Raffinose | − | + | − |
| Melicitose | − | − | − |
| Glycerol | − | − | − |
| Adonitol | − | − | − |
| Mannitol | + | + | + |
| L-Arabinose | + | + | + |
| D-Sorbitol | − | + | − |
| L-Rhamnose | − | − | − |

In the table, "+" indicates positive, "−" indicates negative, and "ND" indicates not determined.

<Mycological Identification>

Based on the mycological properties described above and the sequencing results of the sequence of 16srRNA gene from 5' end to the base at position 1511, homology of 99.7% was found for the standard bacterium strain of *Enterococcus faecium*. As such, the bacterium strain of the invention was identified as *Enterococcus faecium*.

The DNA sequence data of *Enterococcus faecium* NHRD IHARA (i.e., sequence of 16srRNA gene from 5' end to the base at position 1511) is as described below (SEQ ID No. 1).

```
GACGAACGCTGGCGGCGTGCCTAATACATGCAAGTCGTACGCTTCTTT
TTCCACCGGAGCTTGCTCCACCGGAAAAGAAGAGTGGCGAACGGGTG
AGTAACACGTGGGTAACCTGCCCATCAGAAGGGGATAACACTTGGAAA
CAGGTGCTAATACCGTATAACAATCGAAACCGCATGGTTTTGATTTGA
AAGGCGCTTTCGGGTGTCGCTGATGGATGGACCCGCGGTGCATTAGCT
AGTTGGTGAGGTAACGGCTCACCAAGGCCACGATGCATAGCCGACCTG
AGAGGGTGATCGGCCACATTGGGACTGAGACACGGCCCAAACTCCTAC
GGGAGGCAGCAGTAGGGAATCTTCGGCAATGGACGAAAGTCTGACCGA
GCAACGCCGCGTGAGTGAAGAAGGTTTTCGGATCGTAAAACTCTGTTG
TTAGAGAAGAACAAGGATGAGAGTAACTGTTCATCCCTTGACGGTATC
TAACCAGAAAGCCACGGCTAACTACGTGCCAGCAGCCGCGGTAATACG
TAGGTGGCAAGCGTTGTCCGGATTTATTGGGCGTAAAGCGAGCGCAGG
CGGTTTCTTAAGTCTGATGTGAAAGCCCCCGGCTCAACCGGGGAGGGT
CATTGGAAACTGGGAGACTTGAGTGCAGAAGAGGAGAGTGGAATTCCA
TGTGTAGCGGTGAAATGCGTAAATATATGGAGGAACACCAGTGGCGAA
GGCGGCTCTCTGGTCTGTAACTGACGCTGAGGCTCGAAAGCGTGGGGA
GCAAACAGGATTAGATACCCTGATAGTCCACGCCGTAAACGATGAGTG
CTAAGTGTTGGAGGGTTTCCGCCCTTCAGTGCTGCAGCTAACGCATTA
AGCACTCCGCCTGGGGAGTACGACCGCAAGGTTGAAACTCAAAGGAAT
TGACGGGGGCCCGCACAAGCGGTGGGGCATGTGGTTTAATTCGAAGCA
ACGCGAAGAACCTTACCAGGTCTTGACATCCTTTGACCACTCTAGAGA
TAGAGCTTCCCCTTCGGGGGCAAAGTGACAGGTGGTGCATGGTTGTCG
TCAGCTCGTGTCGTGAGATGTTGGGTTAAGTCCCGCAACGAGCGCAAC
CCTTATTGTTAGTTGCCATCATTCAGTTGGGCACTCTAGCAAGACTGC
CGGTGACAAACCGGAGGAAGGTGGGGATGACGTCAAATCATCATGCCC
CTTATGACCTGGGCTACACACGTGCTACAATGGGAAGTACAACGAGTT
GCGAAGTCGCGAGGCTAAGCTAATCTCTTAAAGCTTCTCTCAGTTCGG
ATTGCAGGCTGCAACTCGCCTGCATGAAGCCGGAATCGCTAGTAATCG
CGGATCAGCACGCCGCGGTGAATACGTTCCCGGGCCTTGTACACACCG
CCCGTCACACCACGAGAGTTTATAACACCCGAAGTCGGTGAGGTAACC
TTTTTGGAGCCAGCCGCCTAAGGTGGGATAGATGATTGGGGTGAAGTC
GTAACAAGGTAGCCGTATCGGAA (base at position 1511).
```

<Typing of the Bacterium Strain>

According to the multilocus sequence typing (MLST method) (Non-Patent Document 4) by which a difference among a plurality of gene sequences is patternized and analyzed for each bacterium strain, the typing of the bacterium strain of the invention was carried out. Specifically, by using the publicly available database for MLST method (i.e., MLST.net), the typing within the *Enterococcus faecium* was carried out, and the results are as shown in Table 3. This MLST-type *Enterococcus faecium* was found to be a novel bacterium strain which has not been registered with the database.

TABLE 3

| Name of the Bacterial Strain | Gene Name | | | | | | |
|---|---|---|---|---|---|---|---|
| | AtpA | Ddl | Gdh | PurK | Gyd | PstS | Adk |
| *Enterococcus faecium* JCM1578 | 4 | 3 | 1 | 27 | 1 | 1 | 1 |
| *Enterococcus faecium* NHRD IHARA | 9 | 8 | 8 | 17 | 1 | 19 | 6 |

<Culture Method•Isolation Method>

The bacterium strain *Enterococcus faecium* NHRD IHARA of the invention is the lactic acid bacterium that thrives widely in nature, and the isolation source includes excretions of animals like livestock, various food products and soils. The culture method and isolation method for bacteria are not specifically limited. Medium is not specifically limited if it can be used for bacteria, and culture can be carried out using natural medium, synthetic medium and semi-synthetic medium, etc. As for the medium, those comprising nitrogen source and carbon source are used. Specific examples of the nitrogen source include meat extract, peptone, soybean powder, hydrolyzates of soybean, gluten, casein, yeast extract, and amino acids. Specific examples of the carbon source include glucose, fructose, lactose, sorbitol, inositol, starch syrup, malt extract, starch, bagasse, bran and molasse. In addition to these, as an inorganic substance, ammonium sulfate, potassium phosphate, magnesium chloride, sodium chloride, calcium carbonate, iron, manganese, molybdenum, and various vitamins and others may be added.

The culture temperature is 10 to 50° C. and preferably 25 to 45° C. The culture time is about 6 to 36 hours, and it can be shaken under air or stirred under air. pH of the medium is 3 to 10, and preferably 5 to 7.

With respect to the isolation method, for example, after the culture is completed, the cell bodies are collected and the supernatant is removed by means such as centrifugal isolation and added with distilled water or physiological saline, and after repeating the procedure if required, the cell bodies are collected by centrifugal separation or filtration.

2. With Respect to the Lactic Acid Bacterium Preparation of the Invention

The lactic acid bacterium preparation of the invention includes the type of use as probiotics or fermentation products, and it can be used as a culture liquid itself or after concentration. It is possible to isolate bacteria and use it as vital cell bodies, dead cell bodies or a treated material that is obtained by treatment like heating, drying, freeze-drying, crushing, lysis and extraction.

Specifically, the vital cells isolated according to the invention can be used as they are, or by adding the vital cells to dairy product, fruits, cereal or their processed products (i.e., food products) and fermenting them using lactic acid, they can be used as a fermented product (i.e., treated product).

In addition, according to inactivation of the isolated cell bodies by heating, UV illumination and treatment with formalin, etc., the lactic acid bacterium preparation of the invention can be prepared as a formulation which is suitable for administration. It is also possible that the isolated vital or dead cell bodies are subjected to treatment of grinding and crushing, and after heat-sterilization and sterile filtration of the resulting treated material, if necessary, the filtrate is freeze-dried to give a preparation. The treated product of the cell bodies may be in form of the ground product, crushed product, extract thereof or freeze-dried product, etc.

The lactic acid bacterium preparation of the invention can be used as a single preparation but also can be used as a mixture with other lactic acid bacterium preparations, bifidobacterium preparation and other microbial preparations.

Specific examples of the lactic acid bacterium preparation include the genus *Lactobacillus*, genus *Streptococcus*, genus *Lactococcus*, genus *Leuconostoc*, genus *Pediococcus*, and genus *Enterococcus*. Specific examples of the bifidobacterium preparation include a preparation of bifidobacterium belonging to the genus *Bifidobacterium*. Specific examples of other microbial preparations include preparations of the genus *Bacillus*, genus *Clostridium*, yeast and fungus.

In addition, the lactic acid bacterium preparation of the invention includes not only the mixture of lactic acid bacterium preparations but also the one which contains the co-culture of the lactic acid bacterium of the invention with other microorganisms. Moreover, the lactic acid bacterium preparation of the invention includes a preparation obtained by mixing the lactic acid bacterium of the invention with a substance which increases immunity to synergistically increase the immunity.

3. Use of the Lactic Acid Bacterium Preparation of the Invention

As the lactic acid bacterium preparation of the invention has not only high IgA production-inducing ability but also high enteric colonization rate in the gut, it can provide an increase in immunity by oral administration to a human or livestock. Therefore, an amount efficient for enhancing IgA production can be directly mixed with various food products or feeds for livestock, poultry, nursery fishes or pet animals, or it can be processed as an additive for food and beverage products or animal feeds and used. In particular, when used for the feeds for livestock, it can exhibit an effect of significantly increasing body weight and body weight gain of the livestock and lowering the accident rate. In addition, as an agent for enhancing immune function, it can be used as a pharmaceutical composition for preventing and treating infections in a human or an animal.

Herein, examples of the infections in a human or an animal include, for example, infection in digestive organs, infection in respiratory organs (diarrhea, pneumonia and fever, etc.), and the typical pathogens serving as the cause of the disease include bacteria like pathogenic *E. coli*, bacteria of the genus *Salmonella*, viruses like Influenza, other mycoplasmas, parasites and protozoas.

When it is administered to livestock, for example, typical administration example includes a direct oral administration and a method of mixing with feeds or fluids and administering them. The method of adding it to the feeds is preferable.

When the lactic acid bacterium preparation of the invention is added to a food product, basically every product can be a subject. Examples thereof include a cereal product, a bean product, a meat product, a processed sea product, a dairy product, a snack and a drink.

In addition to being directly added to food products or animal feeds, as an effective component for enhancing IgA production, the "lactic acid bacterium preparation" of the invention can be used in an additive for food products, an additive for animal feeds, or an agent for enhancing immune function, or an agent for preventing and treating infections. In this connection, type of use and use amount will be specifically described below for such cases.

The lactic acid bacterium preparation of the invention can be administered to a human or an animal via any one of the administration routes including oral and parenteral administrations (for example, rectal administration, transdermal administration).

With respect to the preparation, it is possible that cell bodies obtained after culture are separated and concentrated and the original dried powder of the cell bodies can be used by itself as a preparation. Alternatively, it can be prepared as a preparation mixed with any vehicles that are allowed under the Feed Safety Law, like dregs of rice bran oil, wheat flour, glucose, anhydrous silicic acid and wheat bran. In addition, the culture solution in which the cells are cultured as an effective component may be concentrated and dried together with the residues and used as a preparation including the cell bodies. The lactic acid bacterium preparation of the invention is preferably provided in preparation form which is appropriate for the administration route. Examples thereof include an orally administered preparation like a capsule, a tablet, a granule, a powder, a pill, a fine granule and a troche, and a preparation for rectal administration.

In order to ensure the effect of the lactic acid bacterium preparation, it is preferable to carry out the production by appropriately selecting and combining a pharmaceutically acceptable carrier or an additive including a vehicle, an extender, a binding agent, a wetting agent, a disintegrating agent, a surface active agent, a lubricating agent, a dispersing agent, a buffer agent, a preservative, an dissolution aid, a flavor and a fragrance, a pain relieving agent and a stabilizing agent. Examples of the non-toxic additive that can be used include lactose, fructose, glucose, starch, gelatin, magnesium carbonate, synthetic magnesium silicate, talc, magnesium stearate, methyl cellulose, carboxy methyl cellulose or its salt, gum Arabic, polyethylene glycol, syrup, Vaseline, glycerin, ethanol, propylene glycol, citric acid, sodium chloride, sodium sulfite and sodium phosphate.

Examples of the vehicle include saccharides like lactose, D-mannitol, D-sorbitol and white sugar, starches like corn starch and potato starch, and inorganic salts like calcium phosphate, calcium sulfate and precipitated calcium carbonate.

Examples of the disintegrating agent include starches like hydroxypropyl starch, sodium carboxymethyl starch and partially alpharized starch, cellulose derivatives like calcium carboxymethyl cellulose, carboxymethyl cellulose and low-substituted hydroxypropyl cellulose, and other synthetic polymers having polyvinyl pyrrolidone as a cross-linking structure.

Examples of the binding agent include polymers like polyvinyl pyrrolidone, hydroxypropyl cellulose, hydroxypropylmethyl cellulose, gelatin and gum Arabic. Examples of the lubricating agent include those derived from natural products like talc, waxes and light anhydrous silicic acid, and their salts and fatty acids and their metal salts like stearic acid, magnesium stearate, calcium stearate, aluminum stearate and fatty acid ester of sucrose. Moreover, for the tablet, other polymer compounds like Macrogol are suitably used.

It is possible to further add the powder of vehicles to the powder preparations described above. Examples of the vehicle include any vehicles that are allowed under the Feed Safety Law, like defatted rice bran, soybean powder, wheat bran, rice husk, calcium carbonate, sugar, starch, beer yeast and wheat flour. These vehicles can be used singly or in combination of two or more.

With respect to the administration amount of the lactic acid bacterium preparation of the invention, in terms of the effective amount for enhancing IgA production and specifically in the number of cell bodies, $10^8$ to $10^{12}$ cell bodies, and preferably about $10^{10}$ cell bodies can be administered. The content of the lactic acid bacteria in the lactic acid bacterium preparation of the invention is set to have, in terms of dry weight of the cell bodies, 0.05 to 50 mg/g and preferably 5 mg/g. Depending on symptom, age and sex, etc. of the human or animal as an administration subject, it can be appropriately determined within the range of the amount that is effective for enhancing IgA production.

EXAMPLES

Hereinafter, the present invention is explained more specifically in view of the Examples. However, the invention is not at all limited by these Examples.

In addition, the descriptions included in the prior art documents which have been cited herein are incorporated herein as a reference.

Example 1

Screening of *Enterococcus faecium* NHRD IHARA of the Invention

The excretions of livestock and livestock products were diluted 10 times with sterilized physiological saline, and 10 μl of the solution was cultured on BL agar medium for three days. After isolating 400 colonies of the lactic acid bacterium, the bacterium strain forming each colony was temporarily named as NHRD 1 to 400. Further, the term "lactic acid bacterium" used herein refers to the gram-positive and anaerobic bacterium which does not form any catalase and produces an acid in the medium. These isolated lactic acid bacteria were found to be the lactic acid bacteria encompassing various genera such as the genus *Lactobacillus*, genus *Lactococcus*, and genus *Bifidobacterium*, in addition to the genus *Enterococcus*. The name of *Enterococcus faecium* NHRD IHARA related to the invention was given to the bacterium strain which is selected as a bacterium strain showing significantly high IgA production amount according to the test of measuring IgA production amount in which cells of pig Peyer's patch are used for all the lactic acid bacterium strains described above.

Moreover, NHRD IHARA of the invention was internationally deposited with the AIST with the deposit number of FERM BP-11090. Specific descriptions relating to the mycological properties and mycological identification are as described in the above paragraphs [0013] and [0014].

Example 2

Production of Dried Cell Bodies of *Enterococcus faecium* NHRD IHARA (Vital Cells)

*Enterococcus faecium* NHRD IHARA was inoculated to the MRS liquid medium having the composition described below (cell number: $10^2$ cells/ml), and incubated at 37° C. for 16 to 20 hours to obtain the culture medium containing about $10^9$ vital cells/ml. Thus obtained culture medium was centrifuged for 20 minutes at 12,000×g to collect the cells, which were then washed twice with distilled water to give the cell bodies. The resulting cell bodies were suspended in distilled water, and then freeze-dried to give the dried cell bodies (hereinafter, "dried vital cells").

Composition of the MRS liquid medium is described as follows:

| | |
|---|---|
| Pancreatine-digested product of gelatin | 10 g |
| Beef extract | 8 g |
| Yeast extract | 4 g |
| Glucose | 18.5 g |
| Potassium hydrogen phosphate | 3 g |
| Polysorbate 80 (surface active agent) | 1 g |
| Sodium acetate | 3 g |
| Ammonium citrate | 2 g |
| Magnesium sulfate | 0.2 g |
| Manganese sulfate | 0.05 g |
| Distilled water | 1000 ml |

(adjusted to pH 6.2, and heat-sterilized at 121° C. for 15 minutes)

Example 3

Production of Dried Cell Bodies of *Enterococcus faecium* NHRD IHARA (Dead Cells)

The vital cell bodies which had been obtained in the same manner as Example 2 were suspended in distilled water, heated at 100° C. for 30 minutes, and then freeze-dried to give the dried dead cell bodies (hereinafter, referred to as "dried dead cells").

Example 4

IgA Production-Promoting Effect by the Cells of Mouse Peyer's Patch (In vitro Test)

Peyer's patch was harvested from 8 to 12 week old female BALB/c mouse (Japan SLC), and single cells were prepared therefrom by using a cell strainer. In the RPMI medium added with 10% FCS, the cells were prepared to have $1 \times 10^6$ cells/ml and the monolayer was formed on a flat bottom 96 well plate. As an IgA inducing agent, the dried dead cell bodies prepared from the Example 2 or other *Enterococcus faecium* which had been similarly prepared were adjusted to 100 μg/ml and added in an amount of 20 μl, and then cultured for 6 days under shaking. Upon the completion of the culture under shaking, the culture supernatant was collected and the amount of IgA was measured. The culture obtained without adding the dried dead cell bodies to the Peyer's patch was taken as a negative control. The one added with lipopolysaccharide (LPS) instead of the dried dead cell bodies was taken as a positive control. The IgA measurement was carried out by using a commercially available kit (trade name: MOUSE IgA ELISA QUANTITATION KIT, manufactured by Bethyl Laboratories). IgA amount was given as an average value obtained from at least three repeating measurements by using a mouse Peyer's patch.

The amount of IgA in the negative control is used as a standard (1.0), and the comparison of relative ratio (Stimulation Index; S.I.) is shown in FIG. 1A.

As it is shown in FIG. 1A, the IgA relative ratio of the positive control (LPS) is 1 or more, indicating the induction of IgA production. As such, it was found that the method of the invention is useful for the evaluation of the IgA production from a Peyer's patch.

In FIG. 1A, the bacterium strains that belong to the same genus *Enterococcus* were taken as a comparative example and shown in FIG. 1B. All of Comparative example 1 (NHRD44), Comparative example 2 (NHRD88), Comparative example 3 (NHRD99), Comparative example 4 (NHRD102) and Comparative example 5 (NHRD104) belong to *Enterococcus faecium*, while Comparative example 6 (NHRD199) and Comparative example 7 (NHRD326) belong to *Enterococcus faecalis*. Comparative example 8 is obtained by performing the same operations as above for *Enterococcus faecalis* that originates from the commercially available probiotics. In addition, as a reference example, the data of Example 2 of Patent Document 5 (i.e., Enterococcus faecalis NF-1011) obtained under the same experimental condition are also illustrated.

As a result of comparing the IgA production-inducing ability of various *Enterococcus faecium* bacterium strains, it was found that S.I. of *Enterococcus faecium* NHRD IHARA of the invention is 2.6, indicating higher IgA production-inducing ability than the positive control (LPS), and also has an activity of significantly increasing IgA compared to other lactic acid bacteria like other microorganisms of the genus *Enterococcus*, as well as other *Enterococcus faecium*.

Example 5

In Vivo Determination of IgA Production-Inducing Ability

In the current example, *Enterococcus faecium* NHRD IHARA, the bacterium strain of the invention, was orally administered to a mouse and the IgA production amount was measured. Comparison was made among the following four test groups.

(1) Control group 1 (a group to which *Enterococcus faecium* is not administered)

(2) Control group 2 (a group administered with *Enterococcus faecium* in which the S.I is around 1 in Example 3)

(3) A group administered with dried vital cells of *Enterococcus faecium* NHRD IHARA (LA)

(4) A group administered with dried dead cells of *Enterococcus faecium* NHRD IHARA (LAD)

Group (2) to Group (4) were prepared to have the same number of bacterial cells, and mixed in MF powder feed (manufactured by Oriental Yeast Co., Ltd.) to be contained with the weight ratio of 0.33%.

3 week old female BALB/c mice (Japan SLC) were placed to have 9 animals per cage. After pre-raising the animal for 7 days using MF powder feed, the control group 2, LA group and LAD group were switched to the feed that is mixed with *Enterococcus faecium* and were continuously fed with it for 4 weeks. The control group 1 was fed only with MF powder feed.

During the administration period, the body weight of the animal and the feed intake amount were measured for all mice, and any abnormalities in appearance were determined by naked eye. At the time of completion of the administration, the mouse was dissected and the presence of any significant change in the internal organs was determined.

During the administration period, there was no significant difference in the body weight of the mice and the feed intake amount for each test group, and no abnormalities in appearance were found. Moreover, according to the dissection, no significant change in the internal organs was recognized. Based on these results, safety of the bacterium strain of the invention was confirmed.

At the beginning of the administration and four weeks later, feces were collected and the amount of IgA was measured.

The obtained feces were suspended in a buffer solution which weighs ten times compared to the weight of the feces. The suspension was centrifuged under condition including 12,000×g and 4° C. for 5 minutes, and the supernatant was collected to be used as a sample for measuring the amount of IgA. The sample was diluted to optimum concentration and measured by ELISA. The ELISA was carried out in the same manner as the method performed in Example 3.

As the IgA contained in feces originates from intestinal mucosa, the amount of IgA found from the feces was taken as the IgA amount of intestinal mucosa.

The results are shown in FIG. 2.

Among each groups, there was no significant difference in the amount of IgA in the feces at the beginning of the administration. However, four weeks later at which the experiment was terminated (mouse: 8 week old), LA group and LAD group all showed a significant increase compared to the control group ($p<0.01$ for LA group and $p<0.05$ for LAD group). On the other hand, control group 2 shows no significant increase.

Example 6

Test of Applying in the Field of Livestock Breeding (1)

Feed efficiency, body weight gain rate, death rate (accident rate), meat quality and the like are the factors that are directly related to the production cost of livestock products. These factors are expressed otherwise as a productivity of livestock, and recognized as an important indicator for evaluation in livestock management.

In case of livestock, occurrence of a disease like diarrhea causes an increase in accident rate or a decrease in body weight gain rate, yielding reduced productivity. In particular, young animals are prone to suffer from diseases and it results in a significant economic loss.

In the field of livestock breeding, studies to increase the resistance against disease by using immunostimulating effects of lactic acid bacterium have been made (Non-Patent Document 6). One of the probiotic functions of the lactic acid bacterium is the prevention of diarrhea or reduction of accident rate, and various preparations of microorganism including lactic acid bacterium are now commercially available as animal feeds or additive for animal feeds under the name of probiotics.

According to the present example, the IgA production-inducing ability of *Enterococcus faecium* NHRD IHARA, which is the bacterium strain of the invention, was compared to the probiotics that are now commercially available in the field of livestock breeding. After that (Example 7), by using the bacterium strain of the invention in an actual pig farm, it was confirmed that the IgA production-increasing ability is increased and the inhibition on infection by pathogenic microorganism accompanied therewith promotes the increase in productivity.

(6-1) IgA Production-Promoting Activity by the Cells of Pig Peyer's Patch (In Vitro Test)

Peyer's patch was harvested from the small intestine of a pig which had been sacrificed in a slaughterhouse to obtain pork, and the amount of IgA was measured in the same manner as Example 4.

The culture obtained without adding the dried dead cell bodies to the Peyer' s patch cell was taken as a negative control. The one added with LPS (lipopolysaccharide) instead of the dried dead cell bodies was taken as a positive control. The IgA measurement was carried out by using a commercially available kit (trade name: PIG IgA ELISA QUANTITATION KIT, manufactured by Bethyl Laboratories). Considering the difference between individual pigs, IgA amount was given as an average value that is obtained from at least three repeating measurements by using a pig Peyer's patch.

The amount of IgA in the negative control is used as a standard (1.0), and the comparison of its relative ratio (Stimulation Index; S.I.) is shown in FIG. 3.

As it is shown in FIG. 3, the IgA relative ratio of the positive control (LPS) is 1 or more, indicating the induction of IgA production, similar to the mouse Peyer's patch cell. As such, it was found that the method of the invention is useful for the evaluation of the IgA production by using pig Peyer's patch cell.

As a result of comparing the IgA production-inducing ability of various *Enterococcus faecium* bacterium strains, it was found that S.I. of *Enterococcus faecium* NHRD IHARA of the invention is 3.2, indicating higher IgA production-inducing ability than the positive control (LPS), and also has an activity of significantly increasing IgA compared to other *Enterococcus faecium*.

Thus, it was confirmed that the bacterium strain of the invention has high IgA production-inducing ability in livestock, similar to the mouse.

(6-2) Comparison Test with a Commercial Product

The IgA production-inducing ability of the bacterium strain of the invention was compared to the lactic acid bacterium preparations that are commercially available in the field of livestock breeding and other microbial preparations. Determination of IgA amount was made in the same manner as Example 5-1-1. Considering the difference between individual pigs, IgA amount was given as an average value that is obtained from at least three repeating measurements by using a pig Peyer's patch. The results are shown in FIG. 4.

As shown in FIG. 4, it was found that *Enterococcus faecium* NHRD IHARA, which is the bacterium strain of the invention, has significantly higher IgA production-inducing ability compared to the bacterium strains that are used for the microorganism preparations commercially available in the field of livestock breeding.

Example 7

Test of Applying in the Field of Livestock Breeding (2)—Test for Confirming the IgA Production-Inducing Ability and the Effect of Increasing Productivity of Livestock In the present example, in order to determine the IgA production-inducing effect of the bacterium strain of the invention, administration of *Enterococcus faecium* NHRD IHARA was carried out in a general pig farm and the test was performed.

To the feeds for a pig in growth period, dried vital cells of *Enterococcus faecium* NHRD IHARA were added and comparison was made between the following two groups.

(1) Control group 1 (a group to which *Enterococcus faecium* is not administered)

(2) Test group (a group administered with dried vital cells of *Enterococcus faecium* NHRD IHARA)

For Group (2), the cells were prepared to have $10^{10}$ cells per animal per day, and then mixed with the feeds.

25 day-old pork pigs (WLDD) were divided into the control group and the test group (1,200 animals per each group) and raised under the same environmental condition.

(7-1) Test for IgA Production-Inducing Ability

Purpose: To confirm the IgA production-inducing activity in intestinal mucosa and blood serum, feces and blood were collected and the IgA amount was measured. As the IgA contained in feces originates from intestinal mucosa, the amount of IgA found from the feces was taken as the IgA amount of intestinal mucosa. The results are shown in FIG. 5.

As shown in FIG. 5, on the $20^{th}$ day after the administration of the bacterium strain of the invention, the amount of IgA in the intestinal mucosa was significantly increased in the test group. At the time of the completion of the test, the amount of IgA in the blood serum was also increased significantly.

(7-2) Test for Determining Reduction in Occurrence of Disease and Accident Rate

In the present example, a farm attacked by pathogenic *E. coli* which is specific to a pig was taken as a test farm, and 25 day-old pork pigs (WLDD) of the farm were divided into the control group and the test group (1,200 animals per each group) to carry out the test as follows.

The *E. coli* used is referred to as enterotoxigenic *Escherichia coli* (ETEC), which produces an eneterotoxin like heat-stable enterotoxin (ST) and causes diarrhera. The infected animal shows dehydration due to diahhrea and reduction in body weight or body weight gain rate. In a significant case, it may bring death from exhaustion or dying out from significant maldevelopment, eventually yielding an increase in accident rate.

In the present example, to determine the ETEC infection rate, the gene for heat-stable enterotoxin (ST), which is the pathogenic factor of the invention, was detected from animal feces by PCR method. In addition, the staffs of the farm were questioned regarding the clinical signs during the test period, and the final accident rate was determined.

The results are shown in Table 4 and FIG. 6.

As shown in the results, the ETEC infection during the test period was 70% in the control group, while it is inhibited to 33% in the test group in which the accident rate indicating the dying out from exhaustion or significant maldevelopment caused by the infection is low. Furthermore, as a result of questioning the staffs of the farm, it was found that the occurrence of soft feces is lower in the test group compared to the control group.

TABLE 4

| | ST gene | | | |
|---|---|---|---|---|
| | Day 20 of the Test | | End of the test (Day 65) | |
| | Number of positive (N = 10) | Positive ratio (%) | Number of positive (N = 10) | Positive ratio (%) |
| Test group | 0 | 0 | 3 | 33.3 |
| Control group | 0 | 0 | 7 | 70.0 |

(7-3) Test for Confirming the Effect of Enhancing Body Weight and Body Weight Gain Purpose: To verify the effect of enhancing livestock productivity, the body weight and an increase amount of body weight were measured during the test period. The results are shown in FIG. 7.

As shown in FIG. 7, a significant increase in both body weight and body weight gain was recognized after the administration of the bacterium strain of the invention compared to the control group.

Industrial Applicability

When added to food products and animal feeds, etc., it has an effect of enhancing immunity of an animal like human or livestock. In particular, it is useful for increasing body weight and body weight gain of livestock and lowering accident rate therefor. Moreover, as an agent for enhancing the immune function of a human or an animal, it can be used as a pharmaceutical composition for preventing and treating infections.

The invention claimed is:

1. An isolated *Enterococcus faecium* strain NHRD IHARA deposited under FERM number BP-11090.

2. A lactic acid bacterium preparation comprising *Enterococcus faecium* strain NHRD IHARA deposited under FERM number BP-11090 and a pharmaceutically acceptable carrier or additive.

3. A method of producing a lactic acid bacterium preparation according to claim 2, comprising the step of culturing *Enterococcus faecium* strain NHRD IHARA deposited under FERM number BP-11090.

4. The lactic acid bacterium preparation of claim 2 wherein the lactic acid bacterium preparation further comprises other bacteria selected from the group consisting of *Lactobacillus* bacteria, *Streptococcus* bacteria, *Leuconostoc* bacteria, *Pediococcus* bacteria, *Bifidobacterium* bacteria, *Enterococcus* bacteria, *Bacillus* bacteria, and *Clostridium* bacteria.

5. An additive for a food and beverage product comprising the lactic acid bacterium preparation according to claim 2 as an effective component for enhancing immunoglobulin A production in a living body.

6. A food or beverage product comprising the lactic acid bacterium preparation according to claim 2 as an effective component for enhancing immunoglobulin A production in a living body.

7. An additive for animal feeds comprising the lactic acid bacterium preparation according to claim 2 as an effective component for enhancing immunoglobulin A production in a living body.

8. Animal feeds comprising the lactic acid bacterium preparation of claim 2 as an effective component for enhancing immunoglobulin A production in a living body.

9. An agent for enhancing immune function for a human or an animal, comprising the lactic acid bacterium preparation according to claim 2 and a pharmaceutically acceptable carrier or additive.

10. A pharmaceutical composition for preventing or treating an infection in a human or an animal, comprising the lactic acid bacterium preparation according to claim 2 and a pharmaceutically acceptable carrier or additive.

11. A method of increasing body weight of livestock, comprising administering the lactic acid bacterium preparation according to claim 2 to livestock.

12. A method of enhancing body weight gain of livestock, comprising administering the lactic acid bacterium preparation according to claim 2 to livestock.

13. A method of reducing an accident of livestock, comprising administering the lactic acid bacterium preparation according to claim 2 to livestock.

14. A method of improving an immune function of an animal (excluding a human), comprising administering the lactic acid bacterium preparation according to claim 2 to livestock.

15. A method of inhibiting an infection of an animal (excluding a human), comprising administering the lactic acid bacterium preparation claim 2 to livestock.

16. The lactic acid bacterium preparation of claim 2, wherein the *Enterococcus faecium* strain NHRD IHARA deposited under FERM number BP-11090 is a living cell.

17. The lactic acid bacterium preparation of claim 2, wherein the *Enterococcus faecium* strain NHRD IHARA deposited under FERM number BP-11090 is inactivated for growth.

18. A method of increasing body weight of livestock, comprising administering the animal feeds according to claim 8.

19. A method of enhancing body weight gain of livestock, comprising administering the animal feeds according to claim 8.

20. A method of reducing an accident of livestock, comprising administering the animal feeds according to claim 8.

21. The preparation of claim 2, wherein said preparation enhances immunoglobulin A production in a mammal administered said preparation.

* * * * *

```
SEQUENCE LISTING

<160> NUMBER OF SEQ ID NOS: 1

<210> SEQ ID NO 1
<211> LENGTH: 1511
<212> TYPE: DNA
<213> ORGANISM: Enterococcus faecium

<400> SEQUENCE: 1
gacgaacgct ggcggcgtgc ctaatacatg caagtcgtac gcttcttttt ccaccggagc      60
ttgctccacc ggaaaaagaa gagtggcgaa cgggtgagta acacgtgggt aacctgccca     120
tcagaagggg ataacacttg gaaacaggtg ctaataccgt ataacaatcg aaaccgcatg     180
gttttgattt gaaaggcgct ttcgggtgtc gctgatggat ggacccgcgg tgcattagct     240
agttggtgag gtaacggctc accaaggcca cgatgcatag ccgacctgag agggtgatcg     300
gccacattgg gactgagaca cggcccaaac tcctacggga ggcagcagta gggaatcttc     360
ggcaatggac gaaagtctga ccgagcaacg ccgcgtgagt gaagaaggtt ttcggatcgt     420
aaaactctgt tgttagagaa gaacaaggat gagagtaact gttcatccct tgacggtatc     480
taaccagaaa gccacggcta actacgtgcc agcagccgcg gtaatacgta ggtggcaagc     540
gttgtccgga tttattgggc gtaaagcgag cgcaggcggt tcttaagtc tgatgtgaaa     600 gcccccggct caaccgggga gggtcattgg aaactgggag acttgagtgc agaagaggag     660
agtggaattc catgtgtagc ggtgaaatgc gtaaatatat ggaggaacac cagtggcgaa     720
ggcggctctc tggtctgtaa ctgacgctga ggctcgaaag cgtggggagc aaacaggatt     780
agataccctg atagtccacg ccgtaaacga tgagtgctaa gtgttggagg gtttccgccc     840
ttcagtgctg cagctaacgc attaagcact ccgcctgggg agtacgaccg caaggttgaa     900
actcaaagga attgacgggg gcccgcacaa gcggtgggc atgtggttta attcgaagca     960
acgcgaagaa ccttaccagg tcttgacatc ctttgaccac tctagagata gagcttcccc    1020
ttcgggggca aagtgacagg tggtgcatgg ttgtcgtcag ctcgtgtcgt gagatgttgg    1080
gttaagtccc gcaacgagcg caacccttat tgttagttgc catcattcag ttgggcactc    1140
tagcaagact gccggtgaca aaccggagga aggtggggat gacgtcaaat catcatgccc    1200
cttatgacct gggctacaca cgtgctacaa tgggaagtac aacgagttgc gaagtcgcga    1260
ggctaagcta atctcttaaa gcttctctca gttcggattg caggctgcaa ctcgcctgca    1320
tgaagccgga atcgctagta atcgcggatc agcacgccgc ggtgaatacg ttcccgggcc    1380
ttgtacacac cgcccgtcac accacgagag tttataacac ccgaagtcgg tgaggtaacc    1440
```

```
tttttggagc cagccgccta aggtgggata gatgattggg gtgaagtcgt aacaaggtag    1500
ccgtatcgga a                                                         1511
```